United States Patent [19]

Carpenter

[11] Patent Number: 5,418,828
[45] Date of Patent: May 23, 1995

[54] NONDESTRUCTIVE METHOD AND APPARATUS FOR IMAGING GRAINS IN CURVED SURFACES OF POLYCRYSTALLINE ARTICLES

[75] Inventor: Donald A. Carpenter, Lenior City, Tenn.

[73] Assignee: The United States of America as represented by the Department of Energy, Washington, D.C.

[21] Appl. No.: 117,856

[22] Filed: Sep. 8, 1993

[51] Int. Cl.$^6$ .............................. G01N 23/20
[52] U.S. Cl. ........................ 378/71; 378/73; 378/81; 378/74
[58] Field of Search ............. 378/70, 71, 72, 73, 378/74, 79, 81

[56] References Cited

U.S. PATENT DOCUMENTS 4,223,219 9/1980 Born et al. ......................... 378/74
4,364,122 12/1982 Wölfel et al. ...................... 378/73

OTHER PUBLICATIONS

B. K. Tanner, "X-Ray Diffraction Topography," Pergamon Press, New York, N.Y. (1976).
A. Taylor, "X-Ray Metallotraphy," John Wiley & Sons, Inc., New York London (1961).
L. Le Naour, "X-Ray Topography of Uranium Alloys," ORNL-tr-5069, (translated from the French CEA Report, CEA-R-3494), Union Carbide Corp., Nuclear Div., ORNL (May 1968).
Y. Chikauro et al, "Ploycrystal Scattering Topography," J. Applied Crystallography, 15,48 (1982).

*Primary Examiner*—David P. Porta
*Attorney, Agent, or Firm*—David E. Breeden; Stephen D. Hamel; William R. Moser

[57] ABSTRACT

A nondestructive method, and associated apparatus, are provided for determining the grain flow of the grains in a convex curved, textured polycrystalline surface. The convex, curved surface of a polycrystalline article is aligned in a horizontal x-ray diffractometer and a monochromatic, converging x-ray beam is directed onto the curved surface of the polycrystalline article so that the converging x-ray beam is diffracted by crystallographic planes of the grains in the polycrystalline article. The diffracted x-ray beam is caused to pass through a set of horizontal, parallel slits to limit the height of the beam and thereafter. The linear intensity of the diffracted x-ray is measured, using a linear position sensitive proportional counter, as a function of position in a direction orthogonal to the counter so as to generate two dimensional data. An image of the grains in the curved surface of the polycrystalline article is provided based on the two-dimensional data.

15 Claims, 4 Drawing Sheets

NONDESTRUCTIVE METHOD AND APPARATUS FOR IMAGING GRAINS IN CURVED SURFACES OF POLYCRYSTALLINE ARTICLES

The United States Government has rights in this invention pursuant to Contract No. DE-AC05-84OR21400 between the U.S. Department of Energy and Martin Marietta Energy Systems, Inc.

FIELD OF THE INVENTION

The present invention relates to a method and apparatus for determining the grain flow in a curved surface of a polycrystalline article.

BACKGROUND OF THE INVENTION

Although there are a number of established techniques for providing high resolution images of the internal structure of large single crystals, as is discussed below, these techniques are not suitable for verification of the grain flow in a curved or a convex surface of a polycrystalline sample, such as the curved surface of an article made of aluminum. In such an article, the grains of the curved surface of the formed article are flattened during the forming process and are elongated in one direction, with the relatively large faces thereof oriented parallel to the curved surface. It is noted that rotation of these grains about the longitudinal axis into a position perpendicular to the curved surface would make imaging of the grains easier to accomplish but such an approach is undesirable because of the resulting changes in the formed article so produced. On the other hand, the flattened elongated grains of the formed article present special problems insofar as providing high resolution imaging of the grains is concerned.

As mentioned above, there are established methods for providing high resolution images of large single crystals and in this regard, x-ray topography techniques have been used for several years to provide high resolution images of the internal structures of such large single crystals. These methods are used to produce a point-by-point correspondence between the incident x-rays striking the surface and the diffracted x-rays striking a film. Such x-ray topography methods are described, for example, by B. K. Tanner, in "X-Ray Diffraction Topography," Pergamon Press, New York, N.Y. (1976). A further reference in this field which describes x-ray metallography techniques of interest, including the Berg-Barrett method discussed below, is A. Taylor, "X-Ray Metallography," John Wiley & Sons, Inc., New York, London (1961). The Berg-Barrett method just referred to provides for locating the sample a long distance from the x-ray source so that the x-ray beam will appear to be nearly parallel, and then placing the film very close to the sample surface to limit the divergence of the diffracted beam. A Berg-Barrett method has been used for producing images of grains in polycrystalline uranium. This method is described by L. Le Naour, in "X-Ray Topography of Uranium Alloys, ORNL-tr-5069, (translated from the French CEA Report, CEA-R-3494), Union Carbide Corporation, Nuclear Division, Oak Ridge National Laboratory (May 1968). Methods based on crossed-sollor slits for limiting the divergence of the diffracted beam have produced images which show texture variations in rolled aluminum samples. These methods have been described by Y. Chikauro, Y-Yoneda and G. Hiidebrant, in "Polycrystal Scattering Topography," J. Appl. Cryst., 15, 48 (1982).

In each of these methods, parallel and/or divergent x-ray beams are directed toward samples with flat surfaces for diffraction thereby, and these methods can not be used efficiently for imaging grains in a curved polycrystalline surface.

SUMMARY OF THE INVENTION

A principal object of the present invention is to provide an efficient method for determining the grain flow in a convex, textured, polycrystalline surface.

Generally speaking, a first aspect of the invention concerns a method for determining the grain flow of the grains in convex curved surface of a polycrystalline article wherein the method comprises: directing a monochromatic converging X-ray beam onto the curved surface of the polycrystalline article so that the converging beam is diffracted by the grains in that surface of the article; limiting the height of the diffracted beam; measuring the linear intensity of the height-limited diffracted X-ray beam at a plurality of positions along the surface of the article in a direction orthogonal to the width of the beam; and producing an image of the grain flow in the curved surface based on the intensity measurements.

In accordance with a preferred embodiment of the invention, a method is provided for determining the grain flow in a convex surface of a polycrystalline article, wherein the method comprises the following steps or operations:

i) aligning the curved surface of the polycrystalline article in a horizontal x-ray diffractometer;

ii) directing a monochromatic, converging x-ray beam onto the curved surface of the polycrystalline article so that the converging x-ray beam is diffracted by the crystallographic planes of the grains in the polycrystalline article;

iii) passing the diffracted x-ray beam through a set of horizontal, parallel slits;

iv) measuring the linear intensity of the diffracted x-ray beam after the beam passes through the set of horizontal, parallel slits, using a linear position sensitive proportional counter, and as a function of position in a direction orthogonal to the counter; and v) providing an image of the grains in the curved surface of the polycrystalline article based on data from the intensity measurement.

A specific application of the x-ray diffraction imaging method of the invention is in determining the grain flow in a convex, textured, polycrystalline surface of aluminum. In this application, the preferential orientation of the (11 0) crystallographic planes is parallel with the convex surface. However, it will be understood that the method of the invention is not limited to imaging grains in this type of polycrystalline surface.

In accordance with a further aspect of the invention, an apparatus is provided for determining grain flow in a convex curved surface of a polycrystalline article, said apparatus comprising means for producing monochromatic, convergent incident x-ray beam for diffraction by the crystallographic planes in the grains of the polycrystalline article; a set of horizontal, parallel slits for limiting the height of the diffracted beam; a linear position sensitive proportional counter for measuring the linear intensity of the diffracted beam and producing a digital output in accordance therewith; and means for step-scanning the article through the x-ray beam in a direction orthogonal to the counter, i.e., orthogonal to the width of the height-limited beam.

Other features and advantages of the Invention will be set forth in, or apparent from, the following detailed description of preferred embodiments of the invention.

DESCRIPTION OF THE PREFERRED EMBODIMENTS

Figure 1A:
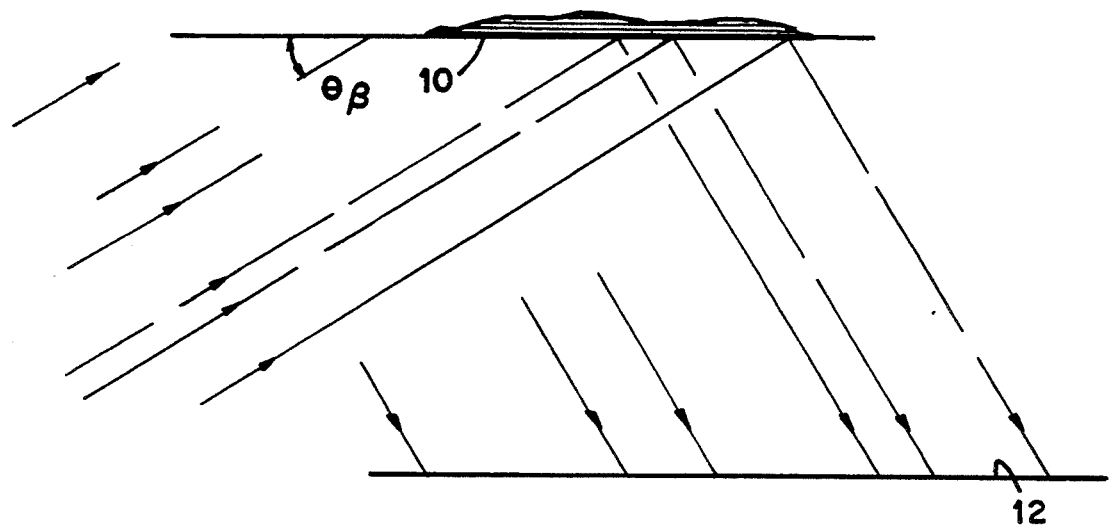
FIG. 1(a) is a schematic drawing showing x-rays diffracting from grains in a polycrystalline sample with a flat surface, wherein a parallel x-ray beam is used for diffraction.

Before considering method and apparatus of the present invention, certain other approaches or techniques will be considered. Referring to FIG. 1(a), the grains in a flat polycrystalline sample 10 are imaged using the Berg-Barrett technique referred to above, with the incident parallel beams of light being diffracted by surface 10 on a film 12. In FIG. 1 (a) (and FIG. 1 (b)) the angle $\theta_\beta$ represents the Bragg angle, required for compliance with Bragg's Law, which is given by the equation $\gamma = 2$ d sin $\theta$, wherein $\gamma$ equals the radiation wavelength, d equals the d-spacing, or distance between diffracting planes, and the angle $\theta$ equals the angle between the incident x-ray beam and the crystal planes in the sample.

Figure 1B:
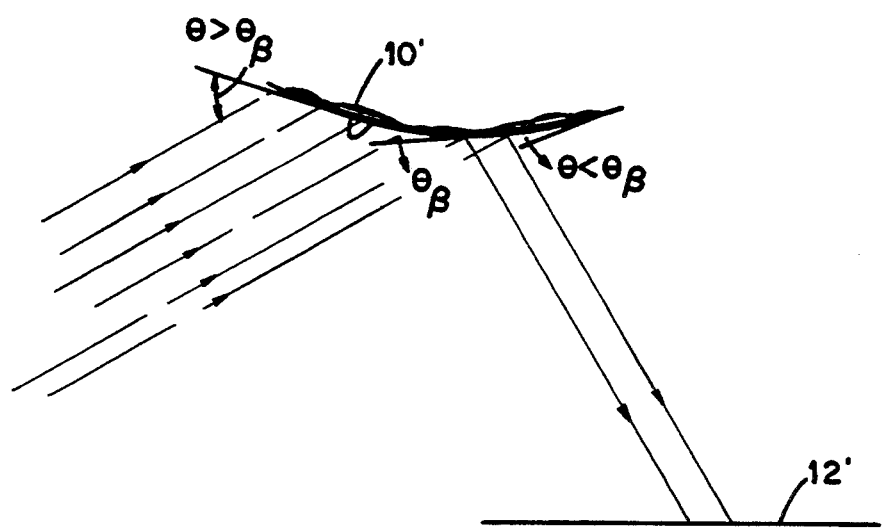
FIG. 1(b) is a schematic drawing showing x-rays diffracting from grains in a polycrystalline sample with a curved surface, wherein a parallel x-ray beam is used for diffraction.

Referring to FIG. 1(b), the same technique is used with a convex specimen surface 10'. FIG. 1(b) indicates that only the preferentially-oriented crystal planes near the point where angle $\theta$ equals $\theta_\beta$ will diffract from a curved surface of a polycrystalline sample when the usual Berg-Barrett technique is used.

Figure 2:
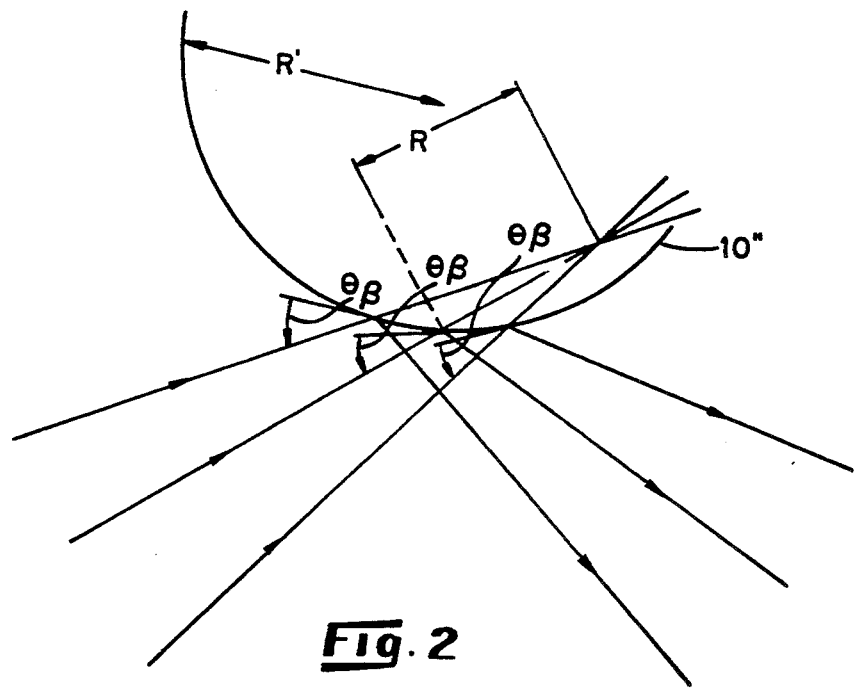
FIG. 2 is a schematic drawing illustrating an aspect of the method of the present invention involving the diffraction of a convergent, monochromatic x-ray beam from a curved surface of a polycrystalline sample.

As stated above, an important aspect of the present invention concerns the use of a convergent incident beam as the incident beam in imaging of the grains. The use of such a convergent incident beam is shown schematically in FIG. 2. The convergent beam can be produced by a commercially available monochromator. In FIG. 2, the position of the curved surface of the sample has been adjusted in accordance with the location of the focal point for the radiation beam so as to limit the incident angle to $\theta_\beta$. This distance is provided by the equation: $R = R' \sin \theta_\beta$, where R is the distance from the sample surface to the focal point of the radiation beam, R' is the radius of the curved surface of the polycrystalline sample, and $\theta_\beta$ is the angle of diffraction for the crystal planes in the polycrystalline sample.

Figure 3:
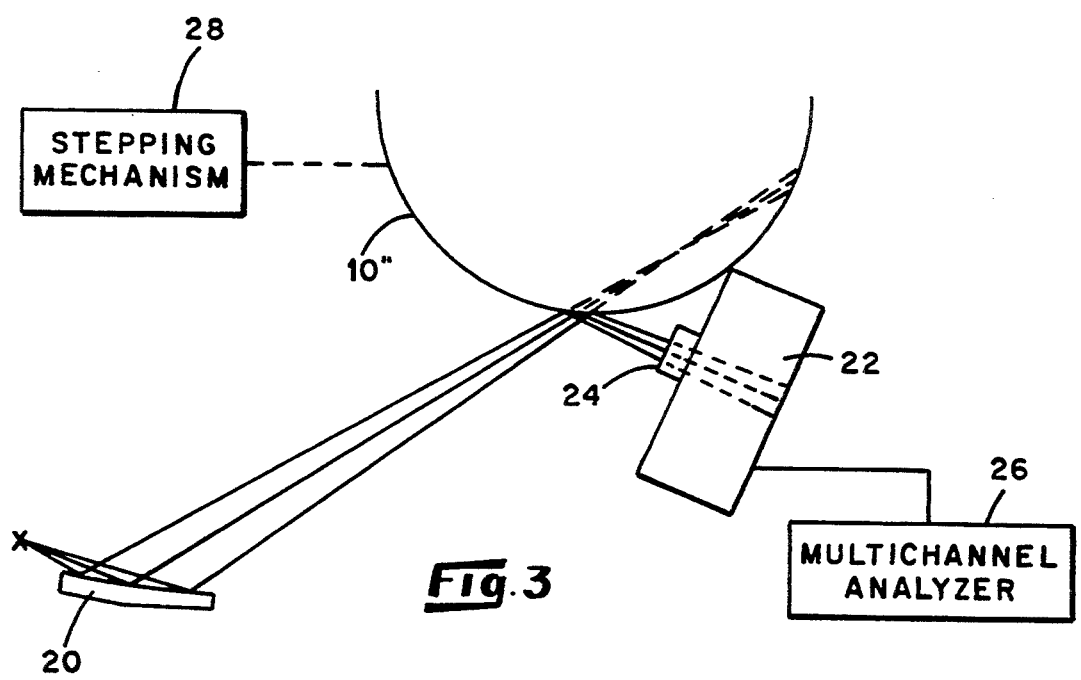
FIG. 3 is a schematic side elevational view, partly in a block diagram format, of one preferred embodiment of the apparatus of the invention.

Before considering FIG. 2 further, reference is now made to FIG. 3, wherein some of the basic components of an apparatus constructed in accordance with a preferred embodiment of the invention are shown. It will be noted that some of these components or units are shown in somewhat more detail in FIG. 5 which is described below. These components, which are part of a horizontal x-ray diffractometer and are basically conventional, include the crystal 20 of a monochromator (not shown), and a position sensitive detector 22 including a horizontal slit housing 24, i.e., a housing which provides a set of horizontal slits (not shown in FIG. 3) in front of the window (not shown) of the detector 22. A multichannel analyzer 26 is connected to the output of detector 22 while a stepping mechanism or device for stepping the sample 10" in a direction perpendicular to the horizontal plane is indicated at 28. The output signal from the position sensitive detector 22 is a signal whose amplitude is proportional to the position of the x-ray along the detecting element.

The height of the diffracted beam from the polycrystalline sample 10" is limited to a line tangent to the curved surface in the plane of FIG. 2 by using, referring to FIG. 3, the set of horizontal, parallel slits referred to above. As stated, these slits are provided in housing 24 in front of the window (not shown) of the position sensitive detector 22, which preferably comprises a linear-position sensitive proportional counter. As illustrated, the linear position-sensitive proportional counter (detector) 22 is disposed or stationed as close as physically possible to the polycrystalline sample 10". It will be understood that the loss of resolution caused by the divergence of the diffracted beam is limited by closeness of the sample 10" and counter 22. The sample is step-scanned using stepping device 28 in a longitudinal direction from the equator to the pole of the curved surface, and linear-intensity data are produced at each step, these data being representative of grain images.

Considering a specific example, a hemispherical-shaped article was back-extruded from a plate of aluminum alloy for testing the apparatus of the invention. In a back-extrusion operation, the grains in a polycrystalline plate of aluminum alloy are flattened, elongated and oriented preferentially in a position with their flat surface and longitudinal axes parallel to the surface of the hemisphere. The back-extruded hemisphere 10" was aligned in a x-ray diffractometer of the type illustrated in the schematic showing provided in FIG. 3.

In the test, the quartz focusing monochromator (represented in FIG. 3 by monochromator crystal 20) diffracted the incident beam to a focal point about 210 mm from the monochromator crystal 20. The convergent nature of the beam was due to the geometry of the crystal, which is known as Johansson geometry. In Johansson geometry, the diffracting planes of the monochromator crystal are inclined to the surface at approximately 10°. In addition, the diffracting surface is ground with a slight radius and then bent to the same radius. The reflected beam was intercepted by the sample 10", i.e., the hemisphere of the aluminum alloy, at a theta angle of 32.38° which corresponds to the theta angle required for diffraction of the (220) crystal plane. The sample surface was struck with each proton at the same theta angle by properly positioning the sample along the converging incident beam. This ensured diffraction of only those grains which were nearly parallel with the surface.

The vertical divergence of the diffracted beam was limited by passing the beam through a pair of the horizontal slits of the housing 24 prior to entrance of the beam into the linear-position sensitive detector 22. The intensity data from the linear position sensitive detector 22 were collected in the multichannel analyzer 26 in which the channels represented position along the wire in the linear-position sensitive detector 22. These data represented a one dimensional image in the horizontal plane of the grains in which the (110) planes were nearly parallel to the surface. Two-dimensional imaging information was obtained by using stepping mechanism 28 to provide stepping of the sample in a direction perpendicular to the horizontal plane, in steps equal to the vertical divergence of 0.1 millimeter. After converting the channels and steps to x-y positions, the intensity data were used to produce images of the grains.

In the example being considered, the resolution of the data was limited by the resolution of the linear-position sensitive detector 22, by the vertical divergence of the diffracted beam, and by the departure of the diffracted beam from the divergent path, shown in FIG. 3, for the horizontal plane. The resolution for the linear-position sensitive detector 22 is believed to be approximately 0.06 mm. The vertical divergence of the diffracted beam was limited by the set of horizontal slits of housing 24. The mosaic spread, as well as the diffusivity of the (110) texture, determined the extent of departure of the diffracted beam from the horizontal divergent path. As noted above, the detector 22 was stationed as close as physically possible to the sample for minimization of this effect. Photomicrographs of the sample revealed that many grains were as large as 1 to 2 mm. Consequently, it is believed that horizontal slits 0.1 mm in width can be used without significantly compromising the resolution. The step size in the y-direction corresponded to 0.108 mm, while each channel in the multichannel analyzer (1024 channels) represented 0.117 mm in the x-direction. The counting time at each step was 1200 seconds.

Figure 4B:
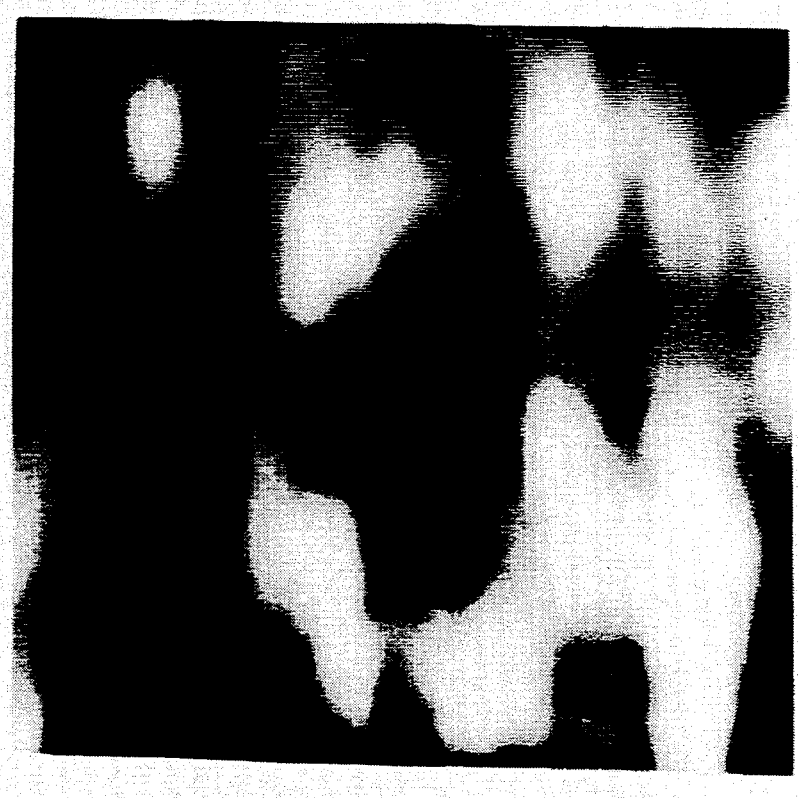
FIG. 4b is a gray-scale image of the intensity data collected using the method and apparatus of the invention in determining the grain flow in a contoured region near the pole of an aluminum hemisphere.
Figure 4A:
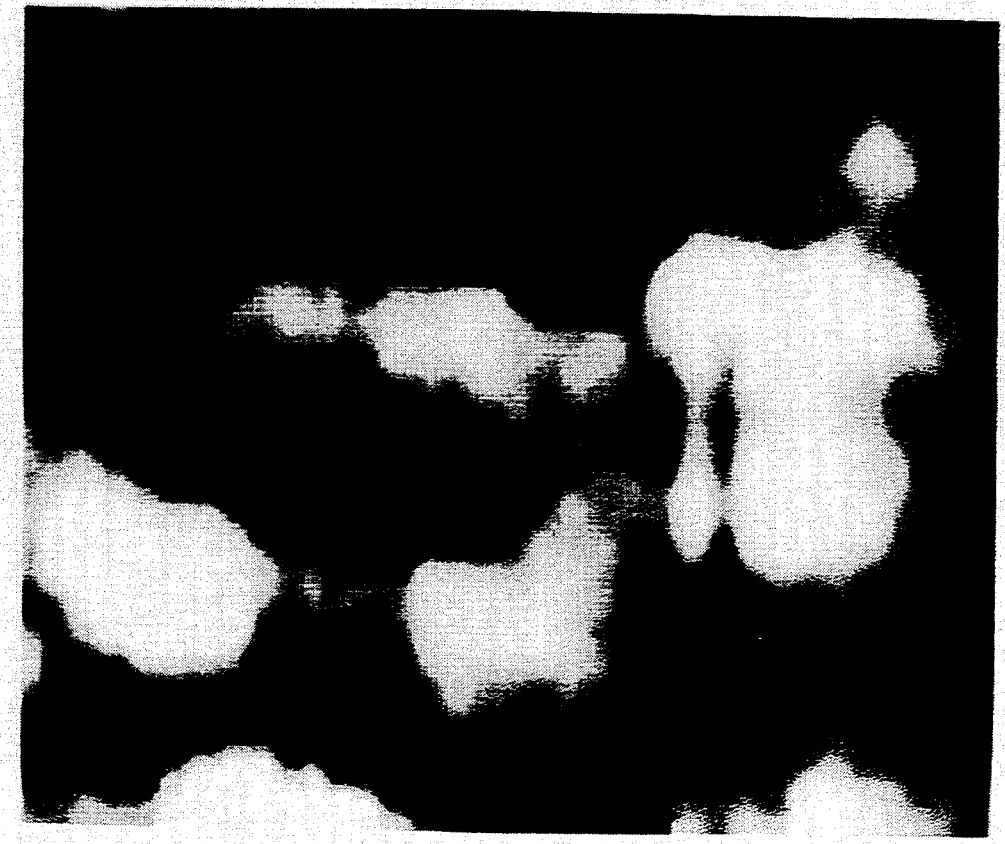
FIG. 4a is a gray-scale image of the intensity data collected using the method and apparatus of the invention in determining the grain flow in a contoured region near the equator of an aluminum hemisphere.

The sample 10" described above in connection with FIG. 3 was examined in the finished condition near the equator and near the pole. The image of intensity data taken near the equator of the sample is shown in FIG. 4a. The image of intensity data taken near the pole of the sample is shown in FIG. 4b. In the images of FIGS. 4a and 4b the horizontal direction is parallel to the equator and the vertical direction is from the equator to the pole. In the high-intensity regions near the equator of the sample, the grains were relatively large and elongated in the direction of the pole region. However, the grains in the high-intensity regions near the pole of the sample were relatively smaller and nondirectional. In other words, a distinct difference was obtained between the data in grain-flow near the equator and near the pole, with the data showing large, flat, elongated grains running parallel with the surface in the equatorial region, while in the polar regions, these grains were rotated so that their elongation directions were perpendicular to the surface, so as to give the appearance of having been flattened in the polar direction. It will be appreciated that quantitative relationships can be developed in terms of grain size and orientation from the data used for the grain flow images.

Figure 5:
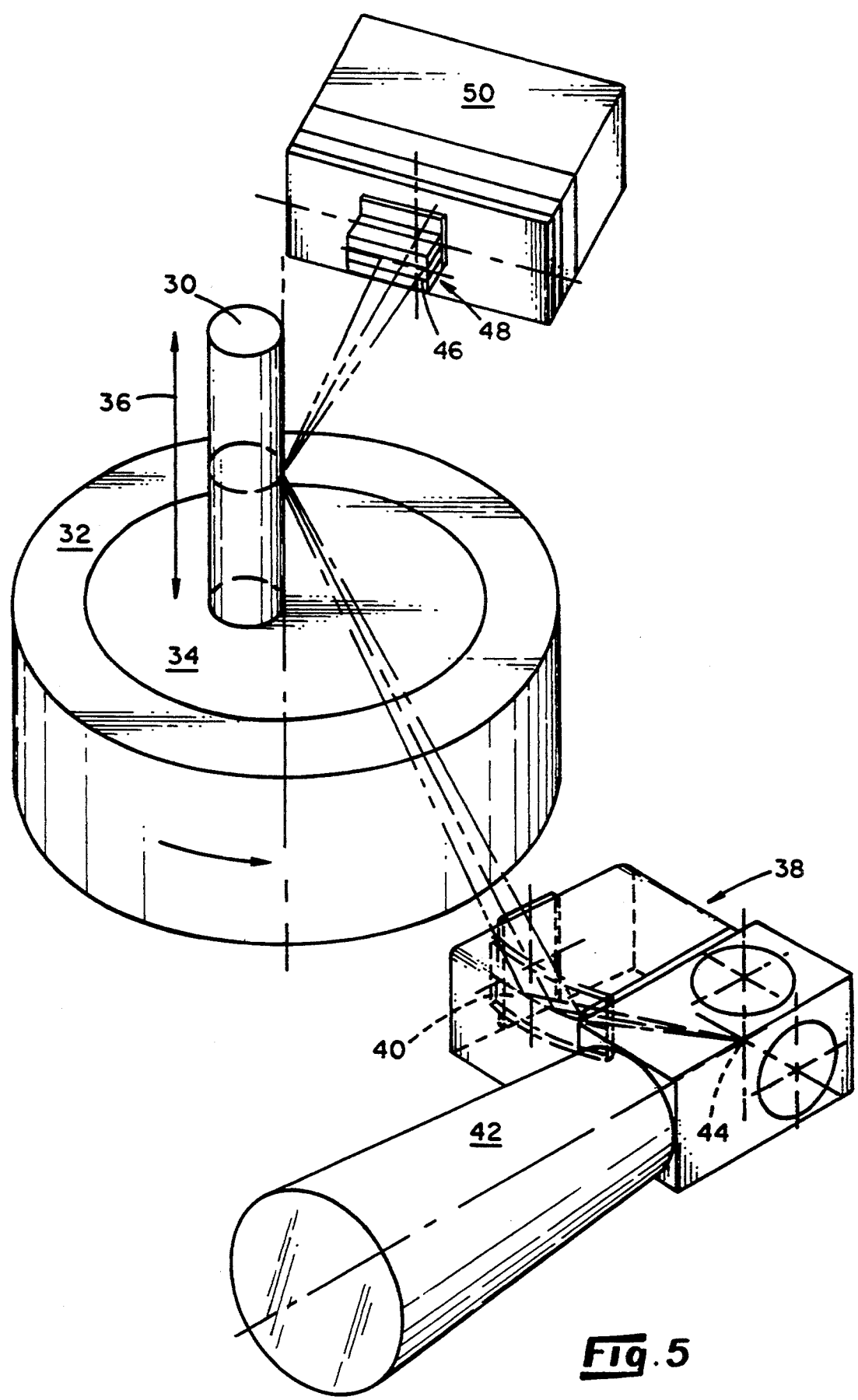
FIG. 5 is a perspective view of an apparatus similar to that of FIG. 3, wherein the sample is cylindrical.

Referring to FIG. 5, an embodiment of the apparatus of the invention is shown which is similar to that of FIG. 3 but shows some of the components of the diffractometer of FIG. 3 in somewhat more detail. In this embodiment, the sample, denoted 30, is cylindrical in shape and is mounted for rotation on a rotary table 32 which includes a stepping mechanism or device, indicated schematically at 34, for providing an up and down stepping movement or motion of the sample 30, as indicated by the double headed arrow 36. A monochromator 38 includes a crystal 40 (corresponding to crystal 20 of FIG. 3) and an associated X-ray tube 42 which provides an X-ray focal spot 44 (corresponding to that of FIG. 3). Beams diffracted by sample 30 are received by the slits, e.g., 46, of a slit array 48 (corresponding to housing 24 of FIG. 3) mounted on the front of a detector 50 (corresponding to detector 22 of FIG. 3). The operation of the apparatus of FIG. 5 is basically the same as described above.

Although the present invention has been described relative to specific exemplary embodiments thereof, it will be understood by those skilled in the art that variations and modifications can be effected in these exemplary embodiments without departing from the scope and spirit of the invention.

What is claimed is:

1. A method for determining the grain flow of the grains in convex curved surface of a polycrystalline article, said method comprising directing a monochromatic converging X-ray beam onto the curved surface of the polycrystalline article so that the converging beam is diffracted by the grains in that surface of the article;

limiting the height of the diffracted beam;

measuring the linear intensity of the height-limited diffracted X-ray beam at a plurality of positions along the surface of the article in a direction orthogonal to the width of the beam; and producing an image of the grain flow in the curved surface based on the intensity measurements.

2. A method as claimed in claim 1 wherein the height of the diffracted beam is limited using an array of parallel, horizontal slits through which the beam is caused to pass prior to measuring the intensity of the beam.

3. A method as claimed in claim 2 wherein the article is stepped through said plurality of positions.

4. A nondestructive method for determining the grain flow of the grains in a convex curved, textured polycrystalline surface, said method comprising the following steps:

i) aligning the convex, curved surface of a polycrystalline article in a horizontal x-ray diffractometer;

ii) directing a monochromatic, converging x-ray beam onto the curved surface of the polycrystalline article so that the converging x-ray beam is diffracted by crystallographic planes of the grains in the polycrystalline article;

iii) causing the diffracted x-ray beam to pass through a set of horizontal, parallel slits;

iv) measuring the linear intensity of the diffracted x-ray beam after passing through the set of parallel slits, using a linear position sensitive proportional counter, as a function of position in a direction orthogonal to the counter to generate two dimensional data; and v) providing an image of the grains in the curved surface of the polycrystalline article from the two-dimensional data.

5. A method as claimed in claim 4 wherein said surface comprises an aluminum surface and the crystallographic planes comprise (110) crystallographic planes oriented parallel to that surface.

6. Apparatus for determining the grain flow of the grains in a convex curved surface of a polycrystalline article, said apparatus comprising:

means for directing a monochromatic converging x-ray beam onto the curved surface of the polycrystalline article toward a focal point beyond said curved surface such that the angle of incidence $\theta$ of said x-ray beam is equal to the angle of diffraction $\theta_\beta$ in accordance with the following relationship $R=R'\sin\theta_\beta$, where R is the distance from said curved surface of the article to the focal point of said converging x-ray beam and R' is the radius of curvature of said curved surface of the article so that the converging beam is diffracted by the grains in said surface of the article;

measuring means for measuring the linear intensity of the diffracted X-ray beam;

means disposed between said article and said measuring means for limiting one dimension of the diffracted beam prior to measurement of the linear intensity of said beam by said measuring means; and movement means for providing relative movement of said article with respect to said measuring means to provide measurement of the linear intensity of the beam at a plurality of positions along the surface of the article.

7. Apparatus as claimed in claim 6 wherein the beam directing means comprises a monochromator and associated x-ray tube.

8. Apparatus as claimed in claim 7 wherein said monochromator includes a monochromator crystal from which x-rays from an x-ray focal spot are directed in the form of said converging x-ray beam onto said surface of said article.

9. Apparatus as claimed in claim 6 wherein said measuring means comprises a linear position sensitive proportional counter.

10. Apparatus as claimed in claim 9 wherein said dimension is height and wherein said movement means comprises means for providing relative movement of said article and said measurement means in direction orthogonal parallel to said height of the beam.

11. Apparatus as claimed in claim 6 wherein said dimension is height and the dimension limiting means comprises an array of parallel horizontal slits.

12. Apparatus as claimed in claim 11 wherein said measuring means comprises a linear position sensitive proportional counter.

13. Apparatus as claimed in claim 12 wherein said measuring means further comprises a multichannel analyzer connected to the output of said counter.

14. Apparatus as claimed in claim 11 wherein said movement means comprises stepping means for stepping said article through said plurality of positions.

15. Apparatus as claimed in claim 6 wherein said movement means comprises stepping means for stepping said article through said plurality of positions.

* * * * *